(12) United States Patent  
Hamel et al.

(10) Patent No.: US 8,149,108 B2  
(45) Date of Patent: Apr. 3, 2012

(54) SYSTEM AND METHOD FOR AUTOMATICALLY POWERING ON AND SYNCHRONIZING A WIRELESS REMOTE CONSOLE TO A CENTRAL CONTROL UNIT SO AS TO ALLOW REMOTE CONTROL OF A MEDICAL DEVICE

(75) Inventors: Andrew J. Hamel, San Mateo, CA (US); Michael G. Hilldoerfer, Mountain View, CA (US); Brannon P. Wells, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 599 days.

(21) Appl. No.: 11/985,339

(22) Filed: Nov. 14, 2007

(65) Prior Publication Data

US 2009/0121865 A1 May 14, 2009

(51) Int. Cl.  
*G08B 1/08* (2006.01)

(52) U.S. Cl. ............... 340/539.1; 340/10.1; 340/10.3; 340/10.34; 340/855.6; 606/1; 606/27; 606/34; 455/343.1

(58) Field of Classification Search ............ 606/1, 27, 606/34; 340/855.6, 539.17, 5.61, 10.34, 340/10.1, 10.3, 539.1; 341/176; 455/343.1  
See application file for complete search history.

(56) References Cited

U.S. PATENT DOCUMENTS

| | | | | |
|---|---|---|---|---|
| 4,005,428 A | * | 1/1977 | Graham | 340/13.28 |
| 4,214,229 A | * | 7/1980 | Warner | 367/198 |
| 4,850,040 A | * | 7/1989 | Teich et al. | 398/112 |
| 5,204,768 A | * | 4/1993 | Tsakiris et al. | 398/107 |
| 5,627,584 A | * | 5/1997 | Nishikori et al. | 348/72 |
| 5,640,151 A | * | 6/1997 | Reis et al. | 340/10.2 |
| 5,767,791 A | * | 6/1998 | Stoop et al. | 340/870.11 |
| 5,850,187 A | * | 12/1998 | Carrender et al. | 340/10.6 |
| 5,855,550 A | * | 1/1999 | Lai et al. | 600/300 |
| 5,874,902 A | * | 2/1999 | Heinrich et al. | 340/10.51 |
| 5,923,373 A | * | 7/1999 | Fukushima | 348/372 |
| 5,938,655 A | * | 8/1999 | Bisch et al. | 606/1 |
| 5,973,611 A | * | 10/1999 | Kulha et al. | 340/5.62 |
| 5,997,528 A | * | 12/1999 | Bisch et al. | 606/1 |

(Continued)

FOREIGN PATENT DOCUMENTS

WO   WO 2005/053248 A1   6/2005

(Continued)

OTHER PUBLICATIONS

International Search Report and Written Opinion of the International Searching Authority, mailed Feb. 2, 2009 (8 sheets).

(Continued)

*Primary Examiner* — Benjamin C Lee  
*Assistant Examiner* — Quang D Pham  
(74) *Attorney, Agent, or Firm* — Flynn, Thiel, Boutell & Tanis, PC (57) ABSTRACT

A system and method for controlling one or more medical devices by a remote console. The remote console communicates wirelessly with a central control unit that connects to one or more of the medical devices. To conserve battery power and simplify operation, the remote console is configured to automatically power on and initiate a wireless connection in response to being brought into proximity of the central control unit. According to another embodiment, the remote console automatically powers on and terminates any previously established wireless connections when brought into proximity of the central control unit.

18 Claims, 5 Drawing Sheets

U.S. PATENT DOCUMENTS

| | | | |
|---|---|---|---|
| 6,074,388 A * | 6/2000 | Tockweiler et al. | 606/34 |
| 6,255,944 B1 * | 7/2001 | Addy | 340/539.3 |
| 6,362,737 B1 * | 3/2002 | Rodgers et al. | 340/572.1 |
| 6,466,131 B1 * | 10/2002 | Tuttle et al. | 340/572.7 |
| 6,509,837 B1 * | 1/2003 | Tuttle et al. | 340/572.7 |
| 6,531,964 B1 * | 3/2003 | Loving | 340/825.72 |
| 6,567,032 B1 * | 5/2003 | Mullaly et al. | 341/176 |
| 6,768,425 B2 * | 7/2004 | Flaherty et al. | 340/870.07 |
| 6,781,508 B2 * | 8/2004 | Tuttle et al. | 340/10.1 |
| 6,791,467 B1 * | 9/2004 | Ben-Ze'ev | 340/12.25 |
| 6,831,562 B2 * | 12/2004 | Rodgers et al. | 340/572.4 |
| 6,874,037 B1 * | 3/2005 | Abram et al. | 709/248 |
| 6,892,052 B2 * | 5/2005 | Kotola et al. | 455/41.2 |
| 6,978,118 B2 * | 12/2005 | Vesikivi et al. | 455/41.1 |
| 7,009,495 B2 * | 3/2006 | Hughes et al. | 340/10.2 |
| 7,010,369 B2 * | 3/2006 | Borders et al. | 700/90 |
| 7,064,675 B2 * | 6/2006 | Zigmond et al. | 340/12.53 |
| 7,079,008 B2 * | 7/2006 | Castle et al. | 340/10.1 |
| 7,079,020 B2 * | 7/2006 | Stilp | 340/506 |
| 7,155,159 B1 * | 12/2006 | Weinblatt et al. | 455/2.01 |
| 7,167,090 B1 * | 1/2007 | Mandal et al. | 340/538.14 |
| 7,224,980 B2 * | 5/2007 | Hara | 455/456.1 |
| 7,229,023 B2 * | 6/2007 | Raskar | 235/492 |
| 7,345,575 B2 * | 3/2008 | Tuttle et al. | 340/10.1 |
| 7,366,934 B1 | 4/2008 | Narayan et al. | |
| 7,496,697 B2 * | 2/2009 | Sween et al. | 710/38 |
| 7,660,420 B1 | 2/2010 | Narayan et al. | |
| 7,737,862 B2 * | 6/2010 | Watanabe | 340/12.51 |
| 2002/0038392 A1 | 3/2002 | De La Huerga | 710/8 |
| 2002/0156466 A1 * | 10/2002 | Sakurai et al. | 606/1 |
| 2003/0007473 A1 * | 1/2003 | Strong et al. | 370/338 |
| 2003/0065805 A1 * | 4/2003 | Barnes, Jr. | 709/231 |
| 2003/0093503 A1 * | 5/2003 | Yamaki et al. | 709/220 |
| 2003/0195644 A1 * | 10/2003 | Borders et al. | 700/90 |
| 2004/0131925 A1 * | 7/2004 | Jenson et al. | 429/61 |
| 2004/0155791 A1 * | 8/2004 | Nguyen et al. | 340/825.69 |
| 2004/0166807 A1 * | 8/2004 | Vesikivi et al. | 455/41.2 |
| 2004/0203352 A1 * | 10/2004 | Hall et al. | 455/41.1 |
| 2004/0205191 A1 * | 10/2004 | Smith et al. | 709/227 |
| 2005/0017727 A1 * | 1/2005 | Oberle | 324/450 |
| 2005/0049458 A1 * | 3/2005 | Honda et al. | 600/118 |
| 2005/0068155 A1 * | 3/2005 | Caruana | 340/10.1 |
| 2005/0080403 A1 * | 4/2005 | Takahashi | 606/1 |
| 2005/0099943 A1 * | 5/2005 | Naghian et al. | 370/229 |
| 2005/0101314 A1 * | 5/2005 | Levi | 455/423 |
| 2005/0121526 A1 * | 6/2005 | Stewart et al. | 235/492 |
| 2005/0143129 A1 | 6/2005 | Funk et al. | |
| 2005/0145129 A1 * | 7/2005 | Holm | 101/415.1 |
| 2005/0154896 A1 * | 7/2005 | Widman et al. | 713/182 |
| 2005/0215233 A1 * | 9/2005 | Perera et al. | 455/411 |
| 2005/0218726 A1 * | 10/2005 | Jenson et al. | 307/116 |
| 2005/0254183 A1 * | 11/2005 | Ishida et al. | 361/18 |
| 2006/0022800 A1 * | 2/2006 | Krishna et al. | 340/10.2 |
| 2006/0038659 A1 * | 2/2006 | Takano et al. | 340/10.51 |
| 2006/0043201 A1 * | 3/2006 | Vesikivi et al. | 235/492 |
| 2006/0044153 A1 * | 3/2006 | Dawidowsky | 340/825.22 |
| 2006/0068750 A1 * | 3/2006 | Burr | 455/343.1 |
| 2006/0103506 A1 * | 5/2006 | Rodgers et al. | 340/10.5 |
| 2006/0116667 A1 * | 6/2006 | Hamel et al. | 606/1 |
| 2006/0119487 A1 * | 6/2006 | Atkinson et al. | 340/825.72 |
| 2006/0145842 A1 * | 7/2006 | Stilp | 340/539.22 |
| 2006/0169771 A1 * | 8/2006 | Brookner | 235/382 |
| 2006/0197660 A1 * | 9/2006 | Luebke et al. | 340/539.26 |
| 2006/0210277 A1 * | 9/2006 | Dubnack et al. | 398/106 |
| 2006/0261950 A1 * | 11/2006 | Arneson et al. | 340/572.1 |
| 2006/0286960 A1 * | 12/2006 | Goehler | 455/403 |
| 2006/0294566 A1 * | 12/2006 | Zlattner | 725/112 |
| 2007/0006275 A1 * | 1/2007 | Wright et al. | 725/133 |
| 2007/0052548 A1 * | 3/2007 | Hankin et al. | 340/825.69 |
| 2007/0057790 A1 * | 3/2007 | Alden et al. | 340/572.1 |
| 2007/0080823 A1 * | 4/2007 | Fu et al. | 340/825.22 |
| 2007/0087719 A1 * | 4/2007 | Mandal et al. | 455/299 |
| 2007/0120650 A1 * | 5/2007 | Nagai et al. | 340/10.2 |
| 2007/0233888 A1 * | 10/2007 | Yamaki | 709/230 |
| 2007/0278998 A1 * | 12/2007 | Koyama | 320/109 |
| 2008/0094245 A1 * | 4/2008 | Hardacker et al. | 340/825.22 |
| 2008/0157993 A1 * | 7/2008 | Du Breuil et al. | 340/825 |
| 2008/0240440 A1 * | 10/2008 | Rose et al. | 380/277 |
| 2008/0303707 A1 * | 12/2008 | Larsen et al. | 341/176 |
| 2009/0048021 A1 * | 2/2009 | Lian et al. | 463/37 |
| 2009/0121865 A1 * | 5/2009 | Hamel et al. | 340/539.17 |

FOREIGN PATENT DOCUMENTS

| | | | |
|---|---|---|---|
| WO | WO 2005/064824 A1 | 7/2005 | |
| WO | WO 2008/098085 A2 | 8/2008 | |

OTHER PUBLICATIONS

U.S. Appl. No. 10/934, 019, filed Sep. 3, 2004 for Multiple-User Voice-Based Control of Devices in an Endoscopic Imaging System, Inventors: S. Hameed, A. Mahadik, K. Javadekar (34 pages).

* cited by examiner

SYSTEM AND METHOD FOR AUTOMATICALLY POWERING ON AND SYNCHRONIZING A WIRELESS REMOTE CONSOLE TO A CENTRAL CONTROL UNIT SO AS TO ALLOW REMOTE CONTROL OF A MEDICAL DEVICE

FIELD OF THE INVENTION

A system and method for controlling one or more medical devices by a wireless remote control, and, in particular, a system and method for automatically powering on a remote control console in response to being brought in proximity to a central controller.

BACKGROUND OF THE INVENTION

Endoscopy is a technology that allows minimally-invasive viewing of internal features of a body. In medicine, endoscopy allows acquisition of high-quality images of internal features of a human body without the need for invasive surgery. The basic tool of endoscopy is the endoscope ("scope"), which is inserted into the body to be viewed. Some endoscopic procedures involve the use of a flexible scope, as in the medical field of gastroenterology, for example. Other medical procedures, such as arthroscopy or laparoscopy, use a rigid scope. The scope is normally coupled to a high-intensity light source that transmits light into the body through the scope, and to a camera head that includes electronics for acquiring video image data. The camera head is typically coupled to a video monitor, which displays video images acquired by the camera.

In endoscopic surgery, various other medical devices may be used, such as an insufflator to pump pressurized gas into body cavities to create more space for viewing and working, an electrocautery tool to stop bleeding, and/or various tools to cut or shape body tissues. These devices are typically controlled remotely by means such as foot pedals and/or switches placed on the floor of the operating room, which are operated by the surgeon. The foot controls may control functions such as on/off, speed or intensity, direction of movement of the tool, mode of operation, etc. The use of foot controls and the like allows the surgeon to adjust various modes and settings of the tools (e.g., speed, intensity) himself, without having to put a tool down, change hands, touch potentially contaminated surfaces with his hands, or take his eyes off the patient.

First generation foot pedals and other types of remote control consoles typically functioned by relaying command signals, in the form of electrical impulses, over a conductive line or cable that physically connected the remote control console to the device being controlled.

As technology advanced, the remote controllers became wireless, thereby allowing a remote control console to be located anywhere within the operating room without having to run a cable along the floor. Such wireless remote control consoles (hereafter referred to simply as "remote consoles") are typically configured to communicate wirelessly with a central control unit, which in turn communicates with one or more medical devices that are to be controlled remotely. To ensure the reliability of the wireless communications, and prevent any interference or accidental communication with another nearby wireless device, the remote console is synchronized with the central controller, thereby assuring that the central controller will only acknowledge command signals transmitted by an authorized remote console. The synchronization process typically involves programming the central controller to recognize an identification code that uniquely identifies all wireless communications transmitted by a specific remote console.

One method of pairing or synchronizing a remote console to a central controller involves manually entering a remote console's identification code into the central controller. Some more advanced systems partially automate the synchronization process, whereby the central controller can wirelessly retrieve the identification code of a remote console by, for example, reading an RFID tag or barcode on the console after the console has been placed into a pairing state and brought into proximity of the central controller.

Typical remote consoles are configured to switch off or enter a "sleep" state after a predefined period of inactivity in order to conserve battery power. As a result, when a user wants to synchronize a remote console to a central controller, he or she must first "awaken" or turn on the remote console so that the console can communicate with the central controller and undergo the synchronization process. Typically a remote console is turned on through some form of user interaction, such as, for example, the depressing of one or a sequence of buttons on the remote console.

Alternatively, a remote console may be configured to not turn off but instead enter a "semi-awake" state where the console continues to consume battery power, albeit at a lower level, thereby allowing the remote console to detect the initiation of the synchronization process and subsequently place itself in a full "awake" state. However, according to this later scheme, the remote console continues to draw battery power even when not in use, thereby significantly reducing the battery life of the console.

The safety of traditional remote consoles can also be compromised due to the failure of a user to "break" any previous wireless connections before implementing a new connection. For example, a remote console is synchronized, and thus wirelessly connected, to a first central controller located in a first operating room. A user then relocates the remote console to a second operating room without first disabling or "breaking" the wireless connection between the remote console and the first central controller, which typically is accomplished through some form of user interaction such as the depressing of one or more buttons on the console. A second user, who is unaware that the first central controller in the first operating room remains wirelessly connected to the remote console, may then synchronize the remote console to a second central controller located in the second operating room. As a result, use of the remote console to control one or more medical devices in the second operating room may lead to erroneous control of one or more medical devices located in the first operating room since the first central controller continues to be responsive to the command signals wirelessly transmitted by the remote console.

Accordingly, what is needed is a remote control console system that can be easily turned on or placed in an "awake" state while requiring either a minimum amount or no user interaction. Also needed is a remote control console system that will reliably and automatically terminate any previous wireless connections before a new wireless connection is established.

BRIEF DESCRIPTION OF THE DRAWINGS

One or more embodiments of the present invention are illustrated by way of example and should not be construed as being limited to the specific embodiments depicted in the accompanying drawings, in which like references indicate similar elements and in which.

DETAILED DESCRIPTION

As described in greater detail below, a single wireless remote console in accordance with the invention (hereafter referred to simply as "console") allows a surgeon or other operator to control one or more medical devices during an endoscopic medical procedure. The console can comprise one or multiple controls designed for operation by an operator's hand or foot to control a medical device or devices.

For illustrative purposes, consider an example of a wireless, foot-operated console that includes one or more foot pedals and/or foot switches to control one or more devices, including a selection switch to allow selection of the device to be controlled if multiple devices are connected. In response to operation of the foot controls, the console transmits signals wirelessly to a central control unit, which causes the central control unit to select a device to be controlled and to control the selected device. The foot control console may include a rechargeable battery, which may be sealed within the console's housing and charged inductively when the console is placed in a docking station. The central control unit and the docking station can be separate units or they can be integrated within a single housing.

I. The Wireless Remote Console and Central Control Unit

Figure 1:
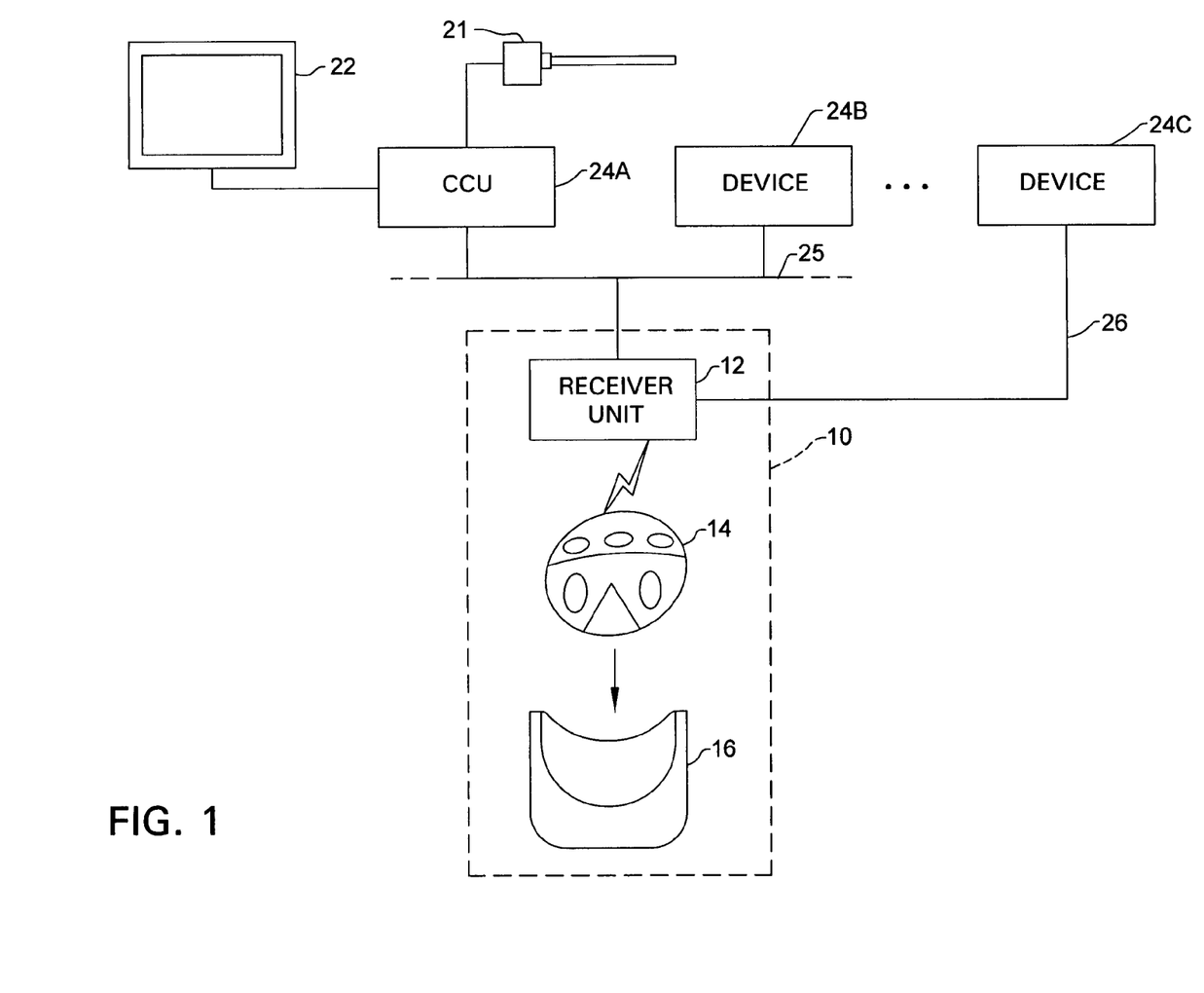
FIG. 1 is a block diagram of a wireless remote control system including a wireless remote console according to certain embodiments of the invention.

FIG. 1 illustrates one example of a wireless remote control system where the remote console 14 is represented by a wireless foot control apparatus in accordance with the invention. The system includes an endoscopic camera 21 connected to a first device 24A comprising a camera control unit (CCU). Also coupled to device 24A is a video monitor 22 to display images acquired by the camera 21. The system also includes a number of different supporting devices 24B, 24C, etc., which may include devices ranging from surgical tools (i.e., an insufflator, an electrocautery tool, a radio frequency generator, or a cutter/shaver tool) to other devices utilized in a surgical or clinical environment (i.e., a video capture device, operating table lights and room lights). Depending on what they are, one or more of devices 24 may be able to connect to each other by a common wired communication medium 25, as are device 24A and device 24B. The wired communication medium 25 may be, for example, an IEEE standard 1394 backplane connection, an Ethernet connection, or other communication medium with similar capability.

Connecting to each of the devices 24, either directly or through the wired communication medium 25, is a central control unit 12 labeled "receiver" in FIG. 1. The remote console 14, represented in FIG. 1 as a wireless foot control apparatus, cooperates with the central control unit 12 to control any of the devices 24 connected to the central control unit 12. Specifically, in this example, console 14 includes various foot operated pedals, switches and/or other foot-operated controls which, when actuated by the operator, cause the console 14 to transmit control signals wirelessly to the central control unit 12. In response to control signals received from the console 14, the central control unit 12 communicates with one of the various devices 24 that is currently selected. This communication may occur over the wired communication medium 25, as would be the case with device 24A or device 24B, or by a direct connection 26 (which may be analog or digital) to the central control unit 12, as would be the case with device 24C. The direct connection 26 may emulate the inputs of a remote control console specific to the device 24C. Furthermore, one or more controlled devices 24 might communicate with the central control unit 12 only via a wireless link.

As the console 14 is wireless, it requires its own power source. According to one embodiment, this power source can be one or more replaceable alkaline batteries. In another embodiment, the power source comprises one or more rechargeable batteries that can be removed from the console 14 for recharging. Alternatively, the rechargeable battery or batteries can be sealed within the housing of the console 14. In such an embodiment, the housing can be made of molded plastic or other similar material, making the console 14 lightweight, durable, soakable, and easy to clean. This approach is desirable because, among other reasons, it is common during certain surgical procedures for considerable amounts of water and/or other fluids to be spilled onto the floor of the operating room. A sealed console housing is advantageous, therefore, since there is no need for electrical contacts that are directly exposed to this operating room environment. In addition, the use of a rechargeable internal battery reduces the number of electrical cables needed in the operating room.

To charge the internal battery, a docking station 16 may be provided. The console 14 is placed into the docking station 16, where the battery is charged by means such as electromagnetic induction. The docking station 16 also serves as a convenient holder for the console 14 when the console 14 is not in use.

Figure 2:
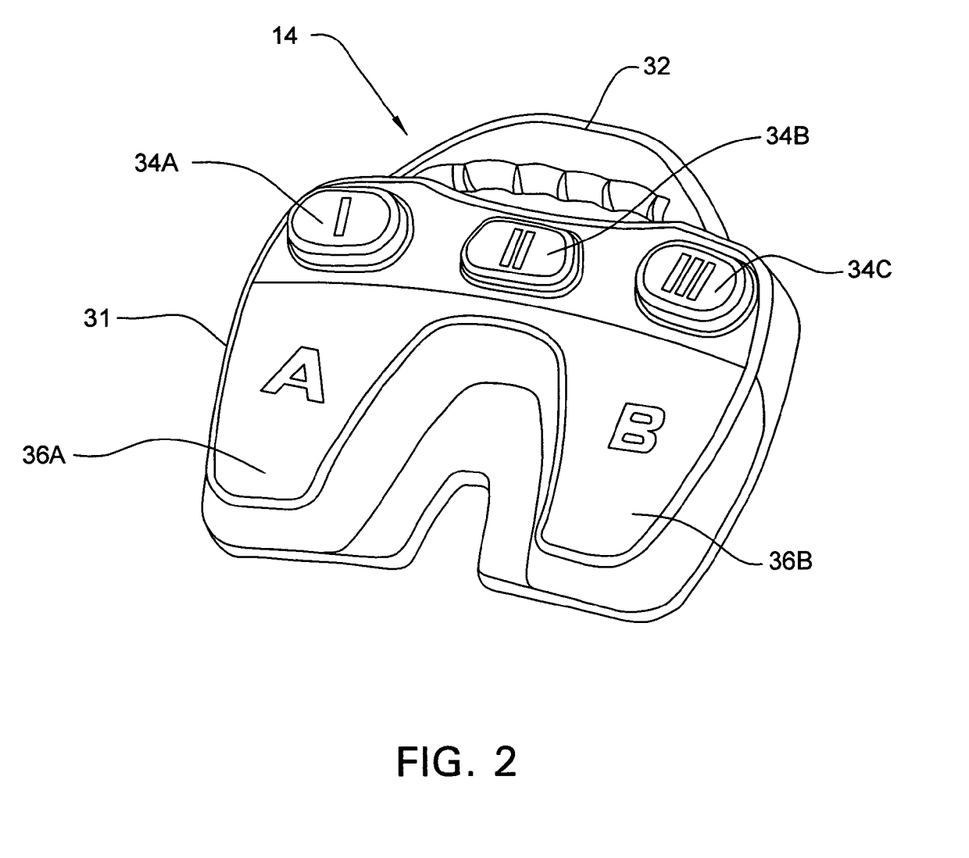
FIG. 2 shows an exterior view of a remote console according to certain embodiments of the invention.

Depicted in the illustrative example of FIG. 2 is an exterior view of one possible type of remote console that can be used in the present invention. Specifically, FIG. 2 depicts a foot-controlled console 14 which is relatively light in weight and includes a handle 32 that allows the console 14 to be conveniently picked up and carried by operating room staff. As shown, the console 14 includes left and right pedals 36A and 36B, respectively, as well as three foot operated switches, i.e., a left switch 34A, a middle switch 34B, and a right switch 34C. Other embodiments may include a different combination of pedals, switches, and/or other controls. The switches 34 may be, for example, simple pushbutton switches and may be used, for example, to select different modes of operation of the various devices 24. The pedals 36A and 36B may be simple potentiometer-type (variable displacement) foot controls, such as for use in controlling the speed, intensity, and/or other variable settings of a medical tool.

For the remainder of the detailed discussion, all references to a remote console 14 will presume to mean a foot-controlled console 14 such as the example illustrated in FIG. 2. However, as previously mentioned, the wireless remote control system of the present invention is not limited to one type or design of wireless remote control console 14, but instead can be configured for use with virtually any type and design of console, including, but not limited to, both foot-operated and hand-operated consoles.

In certain embodiments, the console 14 of FIG. 2, while capable of controlling any of the connected devices 24 of FIG. 1, controls only one device at a time. In such embodiments, one of the switches 34 is used as a selection switch to allow the operator to select the device 24 to be controlled. The function of each of the other controls can vary depending upon which specific device 24 is currently selected to be controlled. The selection can be accomplished by simply pressing the designated selection switch repeatedly to cycle between the different devices 24 connected, either directly or by a communication medium, to the central control unit 12.

In other embodiments, the console 14 is capable of controlling two or more devices simultaneously. For example, two or more separate switches and/or pedals can be used to control two or more separate devices 24 at the same time. Alternatively, the same control on remote console 14 might be used to control two or more devices 24 connected to the central control unit 12.

The central control unit 12 will detect which devices 24 are present or connected to the wired communication medium 25 or by direct connection 26. Therefore, the console 14 does not need to have any knowledge of which device 24 is currently selected, since such knowledge can be maintained entirely within the central control unit 12. The console 14 simply transmits generic control signals, which the central control unit 12 receives and translates into other control signals having the appropriate format and protocol for the device 24 currently selected device for control. In some embodiments, the central control unit 12 can receive input from multiple consoles 14 simultaneously and output the corresponding control signal to either one or multiple devices, depending on if the multiple consoles 14 are controlling the same device or multiple devices.

Figure 3:
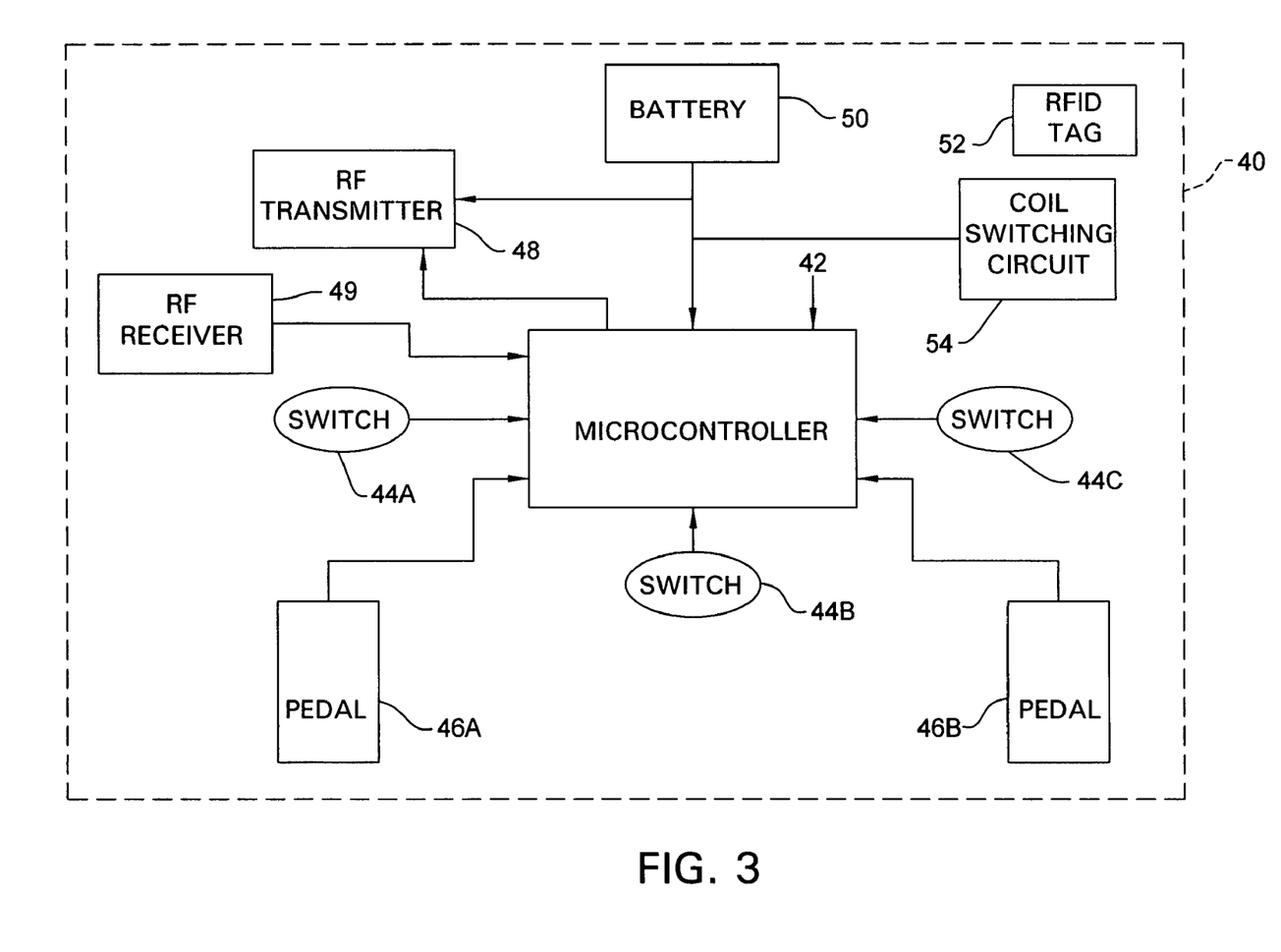
FIG. 3 is a block diagram depicting the components of a remote console according to certain embodiments of the invention.

FIG. 3 shows the components of a wireless remote console 40 according to one exemplary embodiment of the invention. As illustrated, the console 40 includes a conventional programmable microcontroller 42 which couples to a relatively short-range radio frequency (RF) transmitter 48 and RF receiver 49. The RF transmitter 48 and RF receiver 49 can be combined into a single transceiver unit such as, for example, the Cypress WUSB chip set which works within the 2.4 GHz ISM band. In accordance with other embodiments, the console 40 may employ alternate transceiver configurations that operate using other wireless protocols, including 900 MHz RF, Bluetooth, 802.11a/b/g, Ultra-Wide Band (UWB) and Zigbee, as well as non-RF based protocols such as infrared (IR) or laser.

Further included in the console 40 is at least one rechargeable battery 50. Also present is a radio frequency identification (RFID) chip or tag 52 that is either contained within the console 40, or alternatively, fixedly attached to the exterior surface of the console 40. The internal components of the console 40 (i.e., other than the switches and pedals) are completely sealed within the housing of the console 40, which protects those components from damage from the operating room environment and reduces the risk of electrical shock and sparks.

The microcontroller 42 can communicate with the RF transmitter 48 and RF receiver 49 through, for example, a standard RS-232 interface. The RF transmitter 48 transmits control signals to a central control unit, under the control of the microcontroller 42, in response to user inputs applied at the foot operated controls (switches 44A, 44B and 44C and pedals 46A and 46B).

The microcontroller 42 in each wireless console 40 is assigned a unique identification (ID) code. This ID code allows the microcontroller 42 to uniquely identify all the command signals transmitted by the console 40 by incorporating its ID code into the signals it generates and subsequently passes on to the RF transmitter 48. The microcontroller ID code is also stored into a memory of the RFID tag 52, thereby allowing a central control unit to determine the unique identity of the console 40 by wirelessly reading the RFID tag 52.

Also included in the console 40 is a coil switching circuit 54 that is capable of powering the remote console 40 on or off by disrupting the flow of electrical current from the battery 50 to the microcontroller 42. As will be discussed in greater detail below, the coil switching circuit 54 is placed in a "closed" state, thereby permitting the battery 50 to power the microcontroller 42, when the coil switching circuit 54 is subjected to an electromagnetic field (EMF) of a particular frequency or frequencies.

Figure 4:
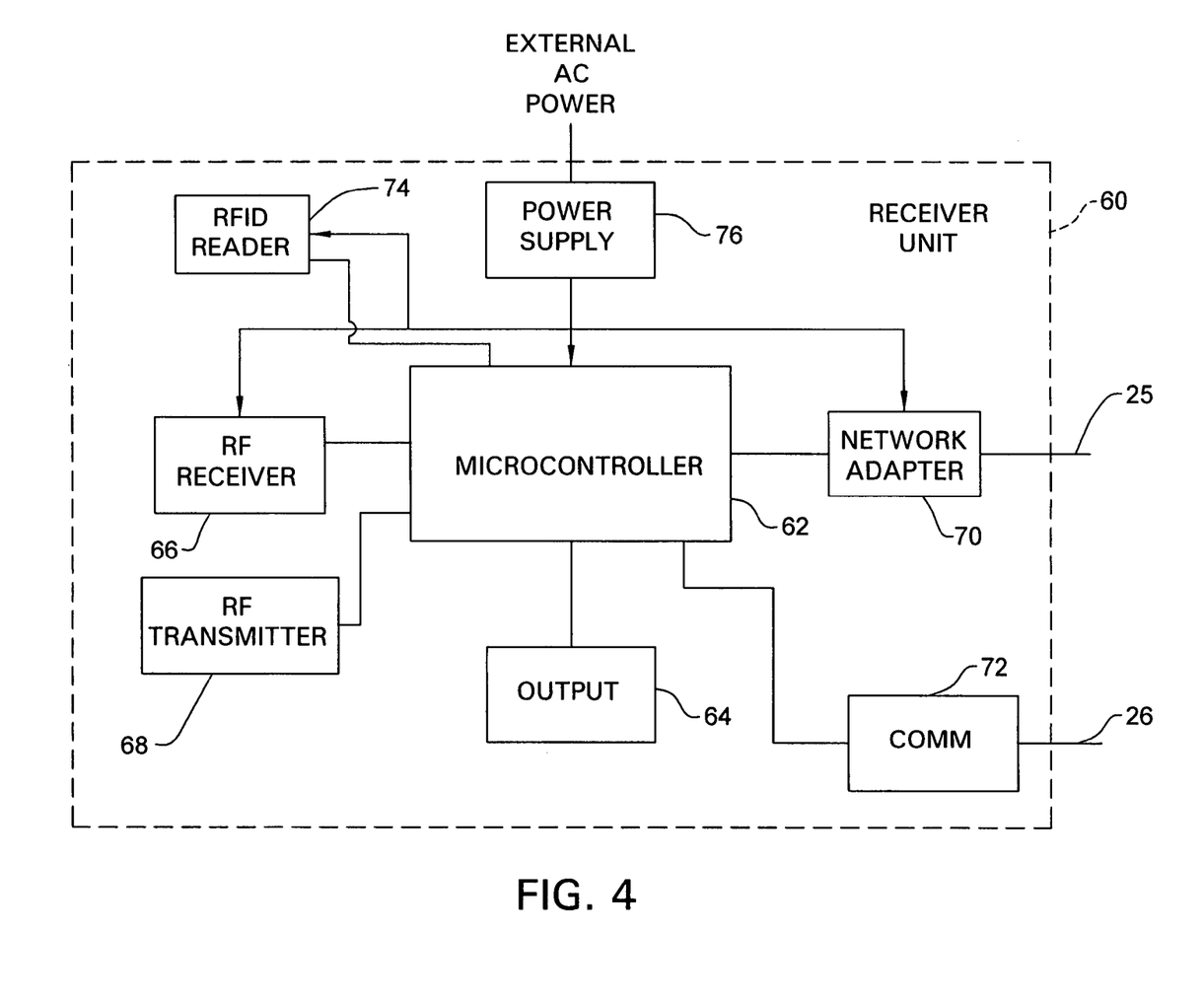
FIG. 4 is a block diagram depicting the components of a central controller according to certain embodiments of the invention.

FIG. 4 is a block diagram of a central control unit 60 according to one embodiment of the invention. As shown, the central control unit 60 includes a programmable microcontroller 62, a wireless receiver 66 and wireless transmitter 68 (or, alternatively, a combined transceiver), a power supply 76, a network adapter 70, and one or more output indicators 64. The microcontroller 62 controls the overall operation of the central control unit 60. The microcontroller 62 may, in other embodiments, be replaced by one or more other forms of control devices capable of performing the same role, such as a programmable general-purpose or special-purpose microprocessor, ASIC, etc. The wireless receiver 66 receives control signals transmitted from the console 40 as described above with respect to FIG. 3, while the wireless transmitter 68 dispatches signals from the central control unit 60 to the wireless console 40. The microcontroller 62 may communicate with the RF receiver 66 and RF transmitter 68 through various means, including, for example, a standard RS-232 interface. The power supply 76 provides regulated power for the central control unit 60, based on power supplied from any available external power source.

Also included within the central control unit 60 is a radio frequency identification (RFID) reader 74 which generates a relatively weak electromagnetic field. When an RFID tag is brought within close proximity to the RFID reader 74, the tag picks up the electromagnetic energy and begins communicating with the RFID reader 74. More specifically, the electromagnetic field being generated by the RFID reader 74 becomes uniquely modulated in a predetermined manner when a RFID tag is in close proximity. It is by this means of modulating an electromagnetic field that the RFID tag communicates information, such as an ID code, to the RFID reader 74.

In addition to communicating information such as ID codes, the electromagnetic field generated by RFID reader 74 can also be utilized as a triggering mechanism for turning on a remote console. As will be discussed in detail below, a remote console 40, such as that depicted in FIG. 3, can be configured to "awaken" or turn on when the coil switching circuit 54 of the console 40 is brought into the presence of the electromagnetic field generated by the RFID reader 74 of the central control unit 60.

The central control unit 60 also includes one or more output indicators 64 which are used to communicate various information to the user of the system, including indicating which device or devices 24 (FIG. 1) are currently selected. The output indicator(s) 64 may include, for example, one or more light-emitting diodes (LEDs), liquid crystal displays (LCDs), audio speakers, or the like.

Depending upon which of the devices 24 is currently selected, the microcontroller 62 uses the control signals received by the wireless receiver 66 to generate commands and/or other control signals directed to a particular device 24 on the wired communication medium 25. The microcontroller 62 is programmed to generate specific commands or other control signals in a format and/or protocol that is appropriate for the currently selected device 24. The microcontroller 62 causes the network adapter 70 to transmit these generated commands onto the wired communication medium 25.

The network adapter 70 can be, for example, a standard IEEE standard 1394 adapter, while the wired communication medium 25 is, for example, an IEEE 1394 backplane. In that case, the central control unit 60 can use standard IEEE 1394 protocols to identify the other devices that are connected to the backplane. In still other embodiments, the central control unit 60 can accommodate communication mediums other than IEEE 1394, such as, for example, connections designed for devices such as the Assignee's Integrated Device Network (SIDNE®) Control System and Total Performance System (TPS), as well as Assignee's Radio Frequency Ablation System (SERFAS™).

In certain embodiments, the central control unit 60 can also (or instead) have one or more "direct" (i.e., non-network) connections 26 to a controlled device 24, as previously mentioned and shown in FIG. 1. In such embodiments, the central control unit 60 includes a communication adapter 72 to couple the microcontroller 62 to the direct connection 26. In certain instances, a direct connection 26 may be implemented as a connection between the central control unit 60 and a device 24 with no other devices or adapters coupled between them, while in other cases, a direct connection 26 may be implemented by connecting the central control unit 60 to a device 24 through a separate, external adapter ("dongle") that emulates the network connection for the central control unit 60.

II. Coil Switching Circuit

As mentioned above, the remote console 40 of FIG. 3 is configured to automatically "awaken" or turn on when the console 40 is brought into proximity of the central control unit 60 so as to be exposed to the electromagnetic field(s) generated by the RFID reader 74 contained within the central control unit 60. This automatic turning on of the remote console 40 in response to exposure of a particular electromagnetic field is the responsibility of the coil switching circuit 54 that is part of the remote console 40.

Figure 5:
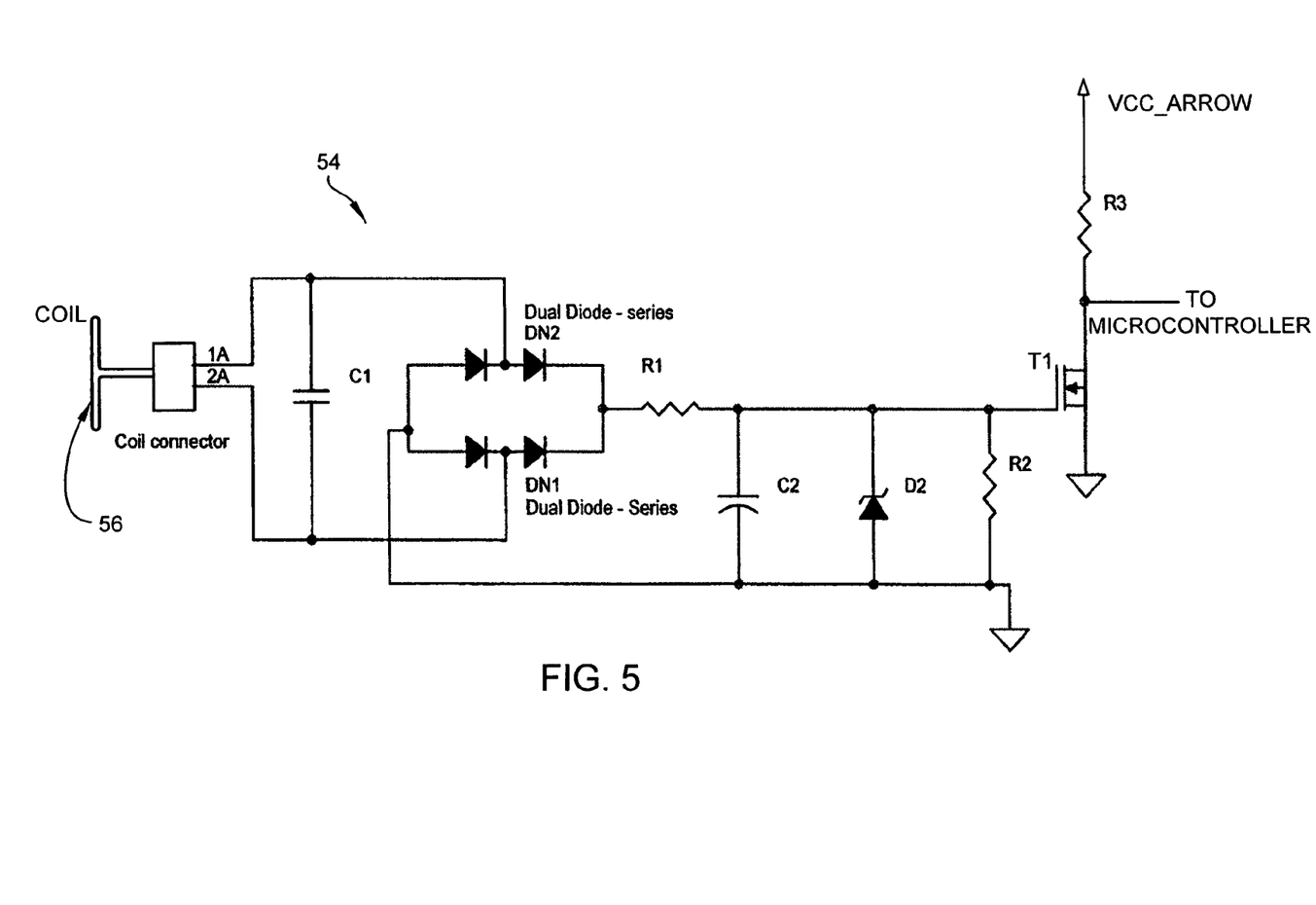
FIG. 5 is a schematic of a coil activation circuit according to certain embodiments of the invention.

FIG. 5 is a circuit diagram of a coil switching circuit 54 according to one embodiment of the invention. As illustrated in FIG. 5, the coil switching circuit 54 comprises a coil 56 for detecting the electromagnetic field generated by the RFID reader 74 when the remote console 40 is brought into proximity of the central control unit 60. It should be noted that coil 56 (hereafter referred to as "secondary coil 56"), is separate from the coil or antenna (hereafter referred to as "primary coil") contained within traditional RFID tags, such as RFID tag 52. Also included in coil switching circuit 54 are capacitors C1 and C2, dual diode series DN1 and DN2 as well as diode D2, resistors R1, R2 and R3, and transistor T1.

Secondary coil 56 is configured or "wound" to have an inductance generally corresponding to the frequency or frequencies of the electromagnetic field generated by the RFID reader 74. As a result, secondary coil 56 is able to detect the electromagnetic field generated by the RFID reader 74, and subsequently cause the remote console 40 to turn on or "wake up" and enter an active state. More specifically, the electromagnetic field generated by the RFID reader 74 induces an electrical current in the secondary coil 56 when the remote console 40 is in proximity to the central control unit 60. The induced electrical current subsequently charges capacitor C1. The voltage differential across capacitor C1 establishes an electrical current that is directed by the dual diode series DN1 and DN2 to flow through resistor R1 and subsequently through the three parallel components comprising capacitor C2, diode D2 and resistor R2. This subsequently establishes a sufficiently large enough voltage differential to cause transistor T1 to switch operating states, resulting in the activation of the remote console 40 and initiation of a wireless connection between the console 40 and central control unit 60.

III. General Operation of the Wireless Remote Control System

According to one embodiment of the invention previously discussed, synchronization between a wireless remote console 40 and central control unit 60 is accomplished by means of radio frequency identification (RFID). Specifically, during the manufacturing process, the unique ID code that is assigned to each microcontroller 42 contained within each console 40 is read or obtained. This unique ID code is then written to a RFID chip or tag 52. This newly written RFID tag 52 is then sealed within or mounted upon the console 40 from which the ID code was first obtained.

In order to synchronize and thus establish a wireless connection between the wireless console 40 and the central control unit 60, a user picks up the console 40, which is "asleep" or powered down, and brings the console 40 next to the central control unit 60. More specifically, the area of the console 40 that contains the RFID tag 52 is aligned with the RFID reader 74 of the central control unit 60. The remote console 40 is then brought into close proximity (e.g., a couple of inches) to the central control unit 60, thereby displacing the secondary coil 56 of the coil switching circuit 54 within the electromagnetic field being transmitted by the RFID reader 74.

The displacement of the remote console 40 into close proximity to the central control unit 60 results in the placement of the secondary coil 56 within the electromagnetic field being transmitted by the RFID reader 74. This leads to the generation of an electrical current in the coil activation circuit 80 due to the secondary coil 56 being configured to have an inductance generally corresponding to the frequency(s) of the electromagnetic field being generated by the RFID reader 74. The amount of electrical current induced in the coil activation circuit 54 is sufficient to activate transistor T1, which subsequently leads to the powering up of microcontroller 42 and the "awakening" of the remote console 40.

Displacement of the remote console 40 into close proximity to the central control unit 60 also results in the placement of the RFID tag 52 within the electromagnetic field being generated by the RFID reader 74. Similar to the coil activation circuit 54, an electrical current is also induced in the RFID tag 52, leading to the generation of a second electromagnetic field by the RFID tag 52. Compared to the first field generated by the RFID reader 74, the second electromagnetic field generated by the RFID tag 52 is modulated to include a signal representing the unique ID code stored in a memory of the RFID tag 52 and representing the ID code of the microcontroller 42 of the remote console 40. The RFID reader 74 detects this second, modulated electromagnetic field being generated by the RFID tag 52, thereby allowing the central controller 60 to wirelessly determine the unique identity of the remote console 40 once it is brought into proximity of the central controller 60.

Accordingly, the act of bringing the remote console 40 into proximity of the central controller 60 results in two initial actions, including the automatic "awakening" or powering up of the remote console 40, and the wireless identification of the remote console 40 by the central controller 60. After the remote console 40 has been identified, the central controller 60 initiates the "pairing" process whereby the remote console 40 and central controller 60 are synchronized so as to establish a reliable wireless connection between them. For additional information on the subsequent "pairing" process, please see U.S. Patent Publication No. US2006-0116667, entitled "Apparatus and Method for Synchronizing A Wireless Remote Control To A Central Control Unit So As To Allow Remote Control Of A Medical Device Over A Secure Wireless Connection", the disclosure of which is herein incorporated by reference in its entirety.

IV. Advantages of a Wireless Remote Control System Containing a Coil Activation Circuit A medical device remote control system according to the embodiments described above provides several advantages over more traditional remote controllers. By utilizing a coil activation circuit 54 such as that depicted in FIG. 5, the remote console 40 can be configured to automatically power on and initiate a wireless connection with the central controller 60. The only action required by a user to initiate the powering on and wireless synchronization sequence is the temporary positioning of the remote console 40 in proximity to the central controller 60. In contrast, more traditional remote control systems either require the remote console to remain powered on in a "semi-awake" state, thereby consuming battery power, or alternatively require a user to manually power on the remote console before initiating a wireless connection.

Unlike more traditional remote control systems such as those utilized in consumer applications and home environments, the system described in the embodiments above possesses the further advantage that it does not require the generation or receipt of a specific command or coded wireless signal to initiate the powering on of the remote console 40. Instead, the remote console 40 automatically powers on simply in response to the presence of an electromagnetic field comprised of one or more predetermined frequencies. Accordingly, the remote console 40 does not need to be programmed to recognize a specific activation or power on command.

The medical remote control system disclosed in the present application provides for a remote console that does not require any electrical contacts on the housing of the console that would be directly exposed to an operating room environment. This allows for a sealed console housing that is soakable or sterilizable. Furthermore, the remote console 40 as described in the embodiments above require no electrical connection between the RFID tag 52 and the internal circuitry that allows the remote console 40 to automatically power on in response to the presence of an electromagnetic field. The use of an electrically isolated RFID tag 52 that can be adhered to the housing of the console, and later removed if necessary, results in a remote console 40 that is easier to manufacture and maintain.

According to an additional embodiment, the coil activation circuit 54 can be configured to automatically power on the remote console 40 while also automatically terminating any previous pairing between the remote console 40 and a central controller 60. As a result, the safety of the remote control system is not affected when a user fails to terminate any previous pairing, and thus fails to break an existing wireless connection with a first central controller 60, before pairing the remote console 40 with a second central controller 60.

V. Additional Embodiments

According to an additional embodiment of the invention, the remote console does not include the coil activation circuit 54 as depicted in FIG. 5, but instead incorporates a reed switch or hall-effect sensor-based circuit that detects the presence of an electromagnetic field. As in the previous embodiments, the remote console is configured to automatically power on and initiate a wireless connection when the console is brought into proximity of the central controller.

According to another embodiment, the system includes a remote console that utilizes one of optical, acoustic and reflective infrared sensing technology to trigger the automatic powering on of the remote console.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A system for controlling at least two medical devices, comprising:

a central control unit in communication with and controlling at least two medical devices;

a remote console having a battery and at least one user-operable control, the remote console configured to wirelessly transmit console command signals to the central control unit indicating a state of the at least one user-operable control for selectively controlling the at least two medical devices;

an identification device associated with the remote console and programmed with an identification code unique to the remote console;

an identification reader associated with the central control unit that 1) automatically wirelessly retrieves the identification code programmed in the identification device and 2) automatically synchronizes the central control unit and the remote console, using an electromagnetic field when the identification device is brought within a predetermined distance of the identification reader; and an activation circuit associated with the remote console separate from the identification device, the activation circuit automatically powering on the remote console with the battery, while the remote console is in an unpowered off state, in response to the inducement of an electrical current in the activation circuit by the electromagnetic field generated by the identification reader associated with the central control unit when the remote console is brought within a predetermined distance.

2. The system according to claim 1, wherein the identification device comprises a radio frequency identification device.

3. The system according to claim 1, wherein the activation circuit is electrically isolated from the identification device.

4. The system according to claim 1, wherein the activation circuit comprises a coil switching circuit including a coil wound to an inductance generally corresponding to a frequency of the electromagnetic field generated by the identification reader.

5. The system according to claim 1, wherein the remote console will automatically terminate any previously established relationships between the remote console and the central control unit in response to the remote console being brought within a predetermined distance of a second central control unit.

6. The system according to claim 1, wherein the central control unit will only process console command signals containing the identification code that corresponds to the remote console with which the central control unit is synchronized.

7. A method of controlling at least one medical device by a wireless connection, comprising the steps of:

providing a remote console with an identification device which is programmed with an identification code unique to the remote console with which the identification device is associated and having at least one user-operable control for remotely controlling at least one function on at least one medical device, the remote console including an activation circuit separate from the identification device and having an off state wherein no power is drawn from a battery of the remote console;

providing a central control unit with an identification reader;

connecting the at least one medical device to the central control unit capable of communicating wirelessly with the remote console;

automatically powering on the remote console with the battery in response to the inducement of an electrical current in the activation circuit of the remote console by an electromagnetic field generated by the identification reader associated with the central control unit by placing the remote console within a predetermined distance of the central control unit;

wirelessly retrieving the identification code from the identification device and automatically wirelessly synchronizing the remote console with the central control unit using the electromagnetic field by placing the remote console within a predetermined distance of the identification reader of the central control unit; and generating with the synchronized remote console at least one wireless remote console command signal that is indicative of a state of the at least one user-operable control.

8. The method according to claim 7, further comprising the step of automatically terminating a previous synchronization between the remote console and the central control unit by placing the remote console within a predetermined distance of a second central control unit.

9. The method according to claim 7, wherein the activation circuit comprises a coil switching circuit that closes to automatically power on the remote console when the induced current is greater than a threshold value.

10. A system for controlling at least two medical devices, comprising:
    a central control unit in communication with and controlling at least two medical devices;
    a remote console comprising a battery, at least one user-operable control and an activation circuit for activating the remote console by supplying power from the battery to the remote console, said remote console being configured to wirelessly transmit console command signals to the central control unit indicating a state of the at least one user-operable control, wherein the remote console, while in an off state drawing no power from the battery, is automatically powered on by the battery in response to the activation circuit being brought within a predetermined distance of the central control unit;
    an identification device associated with the remote console and programmed with an identification code unique to the remote console, said identification device being separate from said activation circuit; and
    an identification reader associated with the central control unit that automatically wirelessly retrieves the identification code programmed in the identification device using an electromagnetic field when the identification device is brought within a predetermined distance of the identification reader and the activation circuit associated with the remote console automatically powers on the remote console with the battery in response to the inducement of an electrical current in the activation circuit by the electromagnetic field generated by the identification reader.

11. The system according to claim 10, wherein said central control unit is connected to each of the at least two said medical devices, and said remote console is configured to wirelessly transmit console command signals to the central control unit that selectively control each of the at least two medical devices.

12. The system according to claim 10, wherein the activation circuit comprises a switching circuit.

13. The system according to claim 12, wherein the switching circuit comprises a coil switching circuit that induces a current to bias a transistor to switch operating states and provide power from the battery to the remote console.

14. The system according to claim 10, wherein the activation circuit comprises a coil switching circuit including a coil wound to an inductance.

15. A system for controlling at least two medical devices by a secure wireless connection, comprising:
    at least two medical devices for use during a medical procedure;
    a remote console comprising:
        at least one user-operable control;
        a battery;
        a transmitter for wirelessly transmitting console command signals indicating a state of the at least one user-operable control and an identification code unique to the remote console;
        an identification device storing the identification code; and
        an activation circuit for powering on the remote console from an off state drawing no power from the battery to an on state by enabling the battery to provide power to the remote console,
    a central control unit in communication with the at least two medical devices comprising:
        a central control unit receiver for receiving the console command signals wirelessly transmitted by the transmitter of the remote console to control the at least two medical devices; and
        an identification reader providing an output to read the identification code of the identification device for automatically placing the central control unit and the remote console in a synchronized state when the remote console is brought within a predetermined distance of the central control unit so as to permit the identification reader to wirelessly retrieve the identification code programmed in the identification device, and the output from the identification reader inducing an electrical current in the activation circuit that automatically powers on the remote console with the battery in response to the output.

16. The system according to claim 15, the identification reader communicating with the identification device separately and independently of the communication between the transmitter of the remote console and the receiver of the central control unit.

17. The system according to claim 15, wherein the identification device comprises a radio frequency identification device that is free from electrical connection to the user-operable control, the battery, the transmitter, and the activation circuit of the remote console.

18. The system according to claim 15, wherein the switching circuit comprises a coil switching circuit that induces a current to bias a transistor to switch operating states and provide power from the battery to the remote console.

* * * * *